United States Patent
Burdinski et al.

(10) Patent No.: US 9,827,351 B2
(45) Date of Patent: Nov. 28, 2017

(54) MEDICAL AND NON-MEDICAL DEVICES MADE FROM HYDROPHILIC RUBBER MATERIALS

(75) Inventors: Dirk Burdinski, Essen (DE); Joyce Van Zanten, Waalre (NL); Lucas Johannes Anna Maria Beckers, Veldhoven (NL); Cornelis Petrus Hendriks, Eindhoven (NL); Willem Franke Pasveer, Dordrecht (NL); Nicolaas Petrus Willard, Valkenswaard (NL); Mareike Klee, Straelen (DE); Biju Kumar Sreedharan Nair, Veldhoven (NL); David Smith, Oakmont, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/127,508

(22) PCT Filed: Jun. 29, 2012

(86) PCT No.: PCT/IB2012/053321
§ 371 (c)(1),
(2), (4) Date: Dec. 19, 2013

(87) PCT Pub. No.: WO2013/001506
PCT Pub. Date: Jan. 3, 2013

(65) Prior Publication Data
US 2014/0134416 A1    May 15, 2014

Related U.S. Application Data

(60) Provisional application No. 61/502,926, filed on Jun. 30, 2011, provisional application No. 61/502,961, (Continued)

(51) Int. Cl.
*A61F 13/15* (2006.01)
*A61L 31/06* (2006.01)
(Continued)

(52) U.S. Cl.
CPC .......... *A61L 31/06* (2013.01); *A61F 5/00* (2013.01); *A61F 13/2002* (2013.01);
(Continued)

(58) Field of Classification Search
CPC ..... A61F 13/2002; A61F 5/00; A61K 8/0208; A61K 8/895; A61K 2800/10;
(Continued)

(56) References Cited

U.S. PATENT DOCUMENTS 3,159,662 A   12/1964  Ashby
3,775,452 A   11/1973  Karstedt
(Continued)

FOREIGN PATENT DOCUMENTS

JP   2006325688 A   12/2006
JP   2008069124 A   3/2008
(Continued)

OTHER PUBLICATIONS

Butts et al. "Silicones" 2003, Encyclopedia of Polymer Science and Technology, pp. 765-841.*
(Continued)

*Primary Examiner* — Maria Veronica Ewald
*Assistant Examiner* — Travis Figg
(74) *Attorney, Agent, or Firm* — Michael W. Haas

(57) ABSTRACT

This invention relates to medical, health care and non-medical devices comprising a rubbery or elastomeric polymer material taking up more than 5% by weight of water and at most 500% by weight of water after immersion in demineralized water at room temperature for a sufficient time to reach saturation. The material may be in the form of
(Continued)

a foam, or in the form of a coating adapted for adhesion to a substrate, or in the form of a sheet, or in the form of a fiber, and may comprise: —repeating units from one or more hydrophobic organic monomers, and —repeating units from one or more monomers (a) being modified with one or more hydrophilic side groups.

14 Claims, 2 Drawing Sheets

Related U.S. Application Data filed on Jun. 30, 2011, provisional application No. 61/586,876, filed on Jan. 16, 2012, provisional application No. 61/586,932, filed on Jan. 16, 2012, provisional application No. 61/586,886, filed on Jan. 16, 2012.

(51) Int. Cl.
| | | |
|---|---|---|
| *C08G 77/392* | (2006.01) | |
| *C08L 83/08* | (2006.01) | |
| *A61F 5/00* | (2006.01) | |
| *A61Q 19/00* | (2006.01) | |
| *A61K 8/895* | (2006.01) | |
| *A61K 8/02* | (2006.01) | |
| *A61L 31/10* | (2006.01) | |
| *A61L 31/14* | (2006.01) | |
| *A61F 13/20* | (2006.01) | |
| *C08G 77/12* | (2006.01) | |

(52) U.S. Cl.
CPC ............ *A61K 8/0208* (2013.01); *A61K 8/895* (2013.01); *A61L 31/10* (2013.01); *A61L 31/146* (2013.01); *A61Q 19/00* (2013.01); *C08G 77/392* (2013.01); *C08L 83/08* (2013.01); *A61K 2800/10* (2013.01); *A61K 2800/54* (2013.01); *A61M 2205/02* (2013.01); *C08G 77/12* (2013.01)

(58) Field of Classification Search
CPC ..... A61K 2800/54; A61L 31/06; A61L 31/10; A61L 31/146; A61M 16/06; A61M 16/0633; A61M 16/0683; A61M 2205/02; A61M 2205/0216; A61M 2205/0222; A61Q 19/00; C08G 77/392; C08L 83/08
USPC ............ 428/219; 521/154; 523/105; 528/30
See application file for complete search history.

(56) References Cited

U.S. PATENT DOCUMENTS

| | | | |
|---|---|---|---|
| 5,861,023 | A | 1/1999 | Vachon |
| 6,062,220 | A | 5/2000 | Whitaker et al. |
| 2002/0160139 | A1 | 10/2002 | Huang et al. |
| 2004/0068057 | A1 | 4/2004 | Kim |
| 2006/0130842 | A1 | 6/2006 | Kleman |
| 2008/0293878 | A1* | 11/2008 | Funk et al. ................... 524/588 |
| 2009/0044810 | A1 | 2/2009 | Kwok et al. |

FOREIGN PATENT DOCUMENTS

| | | | |
|---|---|---|---|
| JP | 2009517515 A | 4/2009 | |
| WO | 9957185 A1 | 11/1999 | |
| WO | 02087645 A1 | 11/2002 | |
| WO | 2007012140 A1 | 2/2007 | |
| WO | WO2007063046 A1 | 6/2007 | |
| WO | 2008070929 A1 | 6/2008 | |
| WO | 2010095105 A1 | 8/2010 | |
| WO | 2010096467 A1 | 8/2010 | |
| WO | WO 2010095105 A1 * | 8/2010 | ............... B01L 3/00 |
| WO | WO2011049919 A1 | 4/2011 | |

OTHER PUBLICATIONS

Hakushi et al. ("A Conductance Study of 1:1 Complexes of 15-Crown-5, 16-Crown-5, and Benzo-15-crown-5 with Alkali Metal Ions in Nonaqueous Solvents" Bull. Chem. Soc. Jpn., 1988, 61, p. 627-632).*
Waker Silicones Elastosil LR.*
"Choosing an Influenza Mask", http://www.crghealthcare.com.au/choosing_a_mask.php, Downloaded on Oct. 7, 2010, 1 Page.
"Face Masks", http://www.cleanroomshop.com/shop/2/12/index.htm, Downloaded Sep. 3, 2010, 4 Pages.
"How the Aegis Microbe Shield Antimicrobial Kills Germs", http://www.breathehealthy.com/about-our-masks/the-breathe-healthy-technology.html, Downloaded Sep. 3, 2010, 2 Pages.
V.P. Barannikov et al, "Molecular Complexes of Crown Ethers in Crystals and Solutions", Russian Journal of Coordination Chemistry, vol. 28, No. 3, 2002, pp. 153-162.
Schneider et al, "Selectivity in Supramolecular Host-Guest Complexes", Chemical Society Reviews, vol. 37, 2008, pp. 263-277.
Creaven et al, "Coordination Chemistry of Calix[4]Arene Derivatives With Lower Rim Functionalisation and Their Appilcations", Coordination Chemistry Reviews, vol. 253, 2009, pp. 893-962.
Steed, "First- and Second-Sphere Coordination Chemistry of Alkali Metal Crown Ether Complexes", Coordination Chemistry Reviews, vol. 215, 2001, pp. 171-221.

* cited by examiner

MEDICAL AND NON-MEDICAL DEVICES MADE FROM HYDROPHILIC RUBBER MATERIALS

CROSS-REFERENCE TO PRIOR APPLICATIONS

This application is the U.S. National Phase application under 35 U.S.C. §371 of International Application Serial No. PCT/IB2012/053321, filed on Jun. 29, 2012, which claims the benefit of U.S. Provisional Application Ser. Nos. 61/502,926, filed on Jun. 30, 2011; 61/502,961, filed on Jun. 30, 2011; 61/586,876, filed Jan. 16, 2012; 61/586,932, filed Jan. 16, 2012; and 61/586,886, filed Jan. 16, 2012. These applications are hereby incorporated by reference herein.

FIELD OF THE INVENTION

The present invention relates to a wide range of medical and non-medical devices comprising hydrophilic rubbery and elastomeric materials in the form of sheets, or foams, or coatings adapted for adhesion to a substrate, or fibers, in particular hydrophilic silicone-based rubber materials having high water uptake capacity. The present invention more specifically relates to a wide range of medical and non-medical devices with water or aqueous fluid absorbing properties comprising hydrophilic silicone-based rubber materials having high water uptake capacity at room temperature.

The present invention more specifically relates to a wide range of medical and non-medical devices comprising biocompatible and non biocompatible polymers and copolymers with water or aqueous fluid absorbing properties, comprising both hydrophobic and hydrophilic monomer units, as bulk materials, as foams, as fibers or as coatings.

BACKGROUND OF THE INVENTION

There are a lot of situations where products with moisture control properties, in particular sweat-absorbing properties, are desired. This applies to medical and health-care applications as well as non-medical applications. Herein-below a few such situations are set forth just for illustrative purposes, i.e. without intention to restrict the technical fields where the present invention has utility.

Apart from medical applications which require gas exchange, e.g. pressure to be applied to the skin of a human, such as respiratory masks and wound dressings, there are other medical applications where sweat-absorbing or aqueous fluid-absorbing properties are desired, and non-medical applications (including industrial applications where water-absorbing properties are desired.

For instance there is a need for non-irritating tight seals for adjusting to a part of the human face such as, but not limited to, nasal plugs and ear plugs, which are more skin compatible and/or can be worn for a longer period of time than nasal plugs and ear plugs known to date.

Nasal plugs are used for absorbing aqueous fluids such as, but not limited to, blood, e.g. for stopping nose bleeds or preventing/treating Von Willebrand's disease. The nasal plug expands upon contact with blood to form a soft, non-abrasive sponge that fits the shape of the nasal cavity. Known nasal plugs made from polyvinyl acetate may also incorporate a pharmaceutically active ingredient to act on the source of bleeding. They have the disadvantage of sticking to the walls of the nose after a prolonged period of time, thus reducing easiness of removal and increasing the risk of renewed bleeding. There is a need in the art for nasal plugs made from other polymer materials where adhesion to the walls of the nose can be controlled in time, thus reducing the risk of renewed bleeding and increasing comfort of the patient.

In the field of external as well as in-ear head sets (ear clips) for e.g. ear phones, audio systems and hearing aids, hydrophobic silicones are used that have the disadvantage of not taking up moisture, thus resulting in the ear head set feeling uncomfortable after a limited period of time. Furthermore with moisture accumulation at the ear skin level, the ear head set easily looses stability. There is a need in the art for an ear head set with increased comfort and stability for the wearer.

Standard materials for catheters include hydrophobic silicones, polyvinyl chloride (PVC), and latex rubber. A problem encountered with hydrophobic silicone catheters e.g. for cardiac and other interventional procedures is the gliding of the material during insertion and moving. There is a need in the art for an improved control of gliding of the catheter, especially when moisture of the surrounding tissue is changing with time. The same need is requested for silicone based medical gloves for medical procedures as for example gynecological procedures were a good gliding is requested or for silicone based condoms.

A more specific problem with urinary catheters is mineral encrustation, which occurs when urease-producing bacteria hydrolyze urea to ammonia making the urine more alkaline. The increased pH results in formation and precipitation of calcium- and magnesium-containing crystals. This mineral deposition can block the catheter eyelet and cause pain during extraction. There is a need in the art for a material reducing mineral encrustation of urinary catheters.

Rubber is used to provide stable grip to all kind of handles such as, but not limited to, a bike handle or a part of a wooden saw handle or a steering wheel or a joystick to give a few examples. If these handles are used for a prolonged period of time (e.g. several hours) and/or outdoors, due to a sweat or rain buildup the rubber handle becomes slippery. There is a need in the art for improving grip stability of handles by absorbing sweat or moisture of the handle material.

There is also a need in the clothing industry for example the shoe industry for improving comfort in clothing wearing, e.g. shoe-wearing, by improving both moisture uptake and prevention of bacteria on textile and non-textile regions in shoes.

There is a need in the art for improving moisture uptake on textile products or fibers such as, but not limited to, sport clothes under heavy sweat conditions, including cotton textiles, to prevent the textile from feeling wet or damp after prolonged use, and thus improving comfort of the textile wearer.

There is a need in the industry for body contact belts, and bands such as wristbands that are applied to the skin for a prolonged period of time, to prevent sweat and give persons a comfortable wearing experience. This can be for example for bands applied around the body or the wrist for wearing sensors for e.g. vital sign monitoring.

There is a need in the industry for body contact regions such as (optionally light weight and/or flame retardant) seats like chairs and armchairs in e.g. airplanes, trains, buses, theaters, conference halls that are used for a prolonged period of time to prevent sweat and give persons a comfortable seating experience.

There is a need in the industry for silicone compositions wherein high amounts of polar compounds such as, but not limited to TiO$_2$ powder, are incorporated into the silicone for applications such as, but not limited to, highly reflective polymer products.

There is also a need in the art for anti-condensation layers and sealing materials with good adhesion on all kind of surfaces such as, but not limited to, metal plates used in the building industry indoors and outdoors and most important with the ability to efficiently stop the growth of living organisms such as, but not limited to, bacteria, fungi or algae.

There is a need in the art for a coating with the ability to efficiently stop the growth of waterborne organisms on the surface (in particular the underwater surface) of boats such as, but not limited to, barnacles and mussels, without having the high toxicity of current tin toxins or copper.

There is a need in the art for long-term sterile skin coatings such as, but not limited to, adhesive bandage, keeping skin highly moisturized. For instance there is a need in the art for a sterile adhesive bandage or coating which, after one day will be completely saturated with water and afterwards will keep a stabilized high humidity necessary to minimize scar formation of a recent wound or to minimize the appearance of old wound scars while at the same time stopping bacterial growth.

In the art of drug delivery there is a need for a rubbery material acting as an ion exchanger for positively charged drugs such as, but not limited to, a transdermal nicotine patch wherein the drug can be slowly released from the rubber material. There is a need in the pharmaceutical art for a rubbery material capable of dissolving a non charged polar drug such as, but not limited to, propranolol (a non selective beta blocker). This is not limited to only drug delivery where the drug is positively charged but using positively charged side groups also negatively charged drugs can be implemented.

There is a need in industry for fast sliding materials for transportation e.g. of goods from position A to position B. Traditional transportation systems in warehouses such as robots are limited in their speed. A sliding system making use of a hydrophilic polymer material sliding on a water film is desirable to enable a high speed transportation system.

There is a need in industry for non-sticking, sliding sealing rings. The current sliding sealing rings are based on hydrophobic polymer material and have a tendency to stick or to slide only at high forces. Hydrophilic rubbery polymer materials such as hydrophilic silicones are desirable to secure seal while a thin water film will give a good sliding behavior.

There is a need in the industry for compatibilizers to mix different types of fewly compatible polymers, in particular thermoplastic polymers, into homogeneous polymer blends. Hydrophilic silicones are desirable as an extra component to improve polymer compatibility and control the morphology of the resulting polymer blends.

There is a need in the industry for dispersing agents for hydrophobic silicones and hydrophobic particles that may be present inter alia in pigments and in water based mixtures such as paints, cosmetic compositions, surfactant compositions and coating compositions.

There is a need for medical grade improved adhesion silicone products and compositions for hair care. Water-absorbing hydrophilic silicones are desirable to improve hair adhesion due to the moisture in the material as well as the presence of polar groups.

There is also a need in the industry for fire inhibiting or flame retardant polymer products which are capable of significantly taking up moisture.

There is a need in industry for printing stents for tampon printing that are inert but able to pick up water based materials. Standard silicones are hydrophobic and therefore are not the optimum material for tampon printing to take up water based compounds such as water based inks. Hydrophilic silicones are thus desirable to solve this problem.

There is a need in industry for biocompatible surfaces for medical diagnosis. Hydrophilic silicones are desirable to make it possible to graft amino-acids, peptides and/or antibodies to their surface especially for use in biochemical and medical analysis.

There is also a need in industry for oil barriers in silicone rings for technical equipment. Hydrophilic silicones are thus desirable to efficiently enable oil stopping and act as a barrier.

There is also a need in industry for improved printing stamps with water-uptake capacity.

The molecular design and synthesis of hydrophilic silicone materials is a relatively unexplored area. Still, some hydrophilic silicone materials have been disclosed in the known prior art. For example, patent application US2002/0160139 discloses a surface modified polymer including a surface that is covalently bonded to a surface modifying compound. Formation of the covalent bond between the polymer and the surface modifying compound is achieved by a reaction between an intrinsic functional group that is present in the polymer and the functional group of the surface modifying compound. By using a polymer having an intrinsic functional group, a separate surface activation step is avoided. Thus, the material has a hydrophilic surface while the bulk of the material remains hydrophobic. Accordingly, this material does not allow for the uptake of moisture through the material and moisture can thus not be removed effectively.

WO 2010/095105 discloses, for use in a microfluidic system, a rubber material comprising polar side groups whereby each of the side groups is linked with the polymer chain of said rubber material via a linker comprising at least 6 atoms. The polar side groups may be ionic side groups such as —$SO_3^-$. For instance the material may be a silicone rubber modified with 15-20 w % sodium alkene $C_{14-16}$ sulfonate. The silicone rubber may have a chain length from 1000 to 10000 Si—O units, and the modified silicone rubber may be made by radical addition of ω-alkenylsulfonic acids to siloxane units present in the polysiloxane chain.

For solving these problems, introduction of an alpha-olefin sulfonate surfactant into biocompatible polymers such as hydrophobic silicones, polybutadiene, polybutadiene-containing polymers, polybutadiene-polyethylene oxides copolymers, poly(meth)acrylates, and isobutylene-ethylene glycol copolymers may be especially relevant. However alpha-olefin sulfonate surfactants, although having a vinyl functional group, do not easily mix with the monomer of commercial polymers like polyethylene (PE), polypropylene (PP), polybutadiene, polyisoprene, polystyrene (PS), polyacetonitrile (PAN), silicones, poly(meth)acrylates, polyacrylonitrile, acrylonitrile-butadiene-styrene copolymers (ABS) and styrene-acrylonitrile copolymers (SAN). This incompatibility can be due to differences in boiling points, making these non volatile surfactants nearly impossible to use in gas phase polymerizations. Even under liquid phase polymerization conditions, it is difficult to mix a hydrophilic surfactant containing a sulfonic acid salt with a hydrophobic monomer or pre-polymer.

There are mainly three industrial crosslinking methods for silicone rubbers. Two of them, the peroxide method and the tin salt initiated cross-linking method, do not give medical grade rubbers and can only be used for non medical applications. The third method, based on platinum salt catalyzed cross-linking, gives medical grade rubber. The peroxide or the platinum salt catalyzed polymerizations are based on vinyl groups. A vinyl containing hydrophilic molecule may be desirable to participate into the cross-linking reaction and give hydrophilic silicone rubbers.

For each of the three cross-linking methods, other reactive groups than vinyl groups can participate. In the peroxide cross-linking method, compounds with unsaturated carbon-carbon bonds, like vinyl, allyl, ethynyl, acrylic or methacrylic can be used. In the tin salt catalyzed cross-linking method, only hydrophilic molecules with hydrolysable silane groups can be used. For the platinum salt catalyzed cross-linking method, vinyl, allyl and ethynyl groups are preferred.

Only in a special case like the suspension polymerization of vinyl chloride in water, can the hydrophilic surfactant be dissolved in a part of the reaction mixture (water) and thus incorporated into the main polymer. However polyvinyl chloride is not regarded as a skin-compatible polymer.

In addition, as outlined hereinabove it is desirable for the candidate material to be easily transformed into a foam and/or to be easily applied in the form of a coating with good adhesion on various types of polymeric and non-polymeric materials.

In front of the above mentioned prior art, there is still a need for a material with hydrophilic bulk properties both in bulk, as a foam or as a coating for use as an aid in moisture control and/or in controlling growth of living organisms and microorganisms.

SUMMARY OF THE INVENTION

It is a first and principal object of embodiments of the present invention to provide a medical or healthcare device selected from the group consisting of tight seals for adjusting to a part of the human face, nasal plugs, ear plugs, sterile bandages, medical cotton (e.g. in the form of gauze, scrub, roll or swab), absorbent pads, catheters, balloons, medical tubings, prosthetic implants, orthotic devices (e;g. a brace), orthodontic devices (e;g. dental impressions and dental molds), medical and surgical wipes (e.g. surgical sponges for eye care), bed sore protection devices, transdermal patches, delivery devices for non-charged polar drugs and positively or negatively charged drugs, anti-scarring plasters, body contact bands, hair care products, and biocompatible surfaces for medical diagnosis or treatment, comprising a rubbery or elastomeric polymer material taking up more than 5% by weight of water, preferably more than 10% by weight of water, more preferably more than 20% by weight of water, most preferably more than 40% by weight of water, and up to 500% by weight, or up to 200%, or 250% by weight, or up to 120% by weight, of water after immersion in demineralized water at room temperature for a sufficient time (such as, but not limited to, 5 days or more) to reach saturation. The rubbery or elastomeric polymer material present in the medical or healthcare device of this invention may be in the form of a foam, a bulk material, a sheet, a fiber or a coating applied onto a substrate, or any other form suitable for the intended medical or health care device.

It is another second and independent object of further embodiments of the present invention to provide a non-medical device comprising a rubbery or elastomeric polymer material taking up more than 5% by weight of water, preferably more than 10% by weight of water, more preferably more than 20% by weight of water, most preferably more than 40% by weight of water, and up to 500% by weight, or up to 200%, or 250% by weight, or up to 120% by weight, of water after immersion in demineralized water at room temperature for a sufficient time (such as, but not limited to, 5 days or more) to reach saturation. The rubbery or elastomeric polymer material present in said non-medical device may be in the form of a foam, a bulk material, a sheet, a fiber or a coating applied onto a substrate, or any other form suitable for the intended non-medical device.

It is yet another third independent object of further embodiments of the present invention to provide suitable foaming silicone compositions comprising:

one or more hydrophobic organic monomers selected from the group consisting of dialkylsiloxanes and diarylsiloxanes, or a silicone precursor, a monomer or polymer with one or more hydrophilic side groups, one or more hydroxylated components, from 1 to 250 ppm of a platinum catalyst, and optionally a foam density-reducing amino component.

It is yet another fourth and independent object of further embodiments of the present invention to provide rubbery or elastomeric polymer materials taking up more than 5% by weight and up to 500% by weight of water after immersion in demineralized water at room temperature for a sufficient time (such as, but not limited to, 5 days or more) to reach saturation, and being in the form of a foam, or in the form of a coating adapted for adhesion to a substrate, comprising:

repeating units from one or more hydrophobic organic monomers, and repeating units from one or more monomers (a) being modified with one or more hydrophilic side groups if our hydrophilic molecule has two or more reactive groups it becomes part of the main chain of the polymer. It is not a side group anymore.

In one specific embodiment of this fourth object of the present invention, the rubbery or elastomeric polymer material may take up more than 10% by weight of water, more preferably more than 20% by weight of water, most preferably more than 40% by weight of water, and up to 200%, or up to 250% by weight, or up to 120% by weight of water after immersion in demineralized water at room temperature for a sufficient time (such as, but not limited to, 5 days or more) to reach saturation. In one specific embodiment of this fourth object of the present invention, the repeating units (b) represent from 1% to 30% of the total number of repeating units (a) and repeating units (b). Such coating materials or foam materials are especially useful as parts or components of the above-referred medical and non-medical devices (first and second objects of the invention), optionally in combination with parts or components comprising other non-polymer or polymer materials.

In one specific embodiment of the present invention, hydrophilic silicone-based rubber materials useful as parts or components of the above-referred medical and non-medical devices (first and second objects of the invention) may comprise:

dialkylsiloxane (preferably dimethylsiloxane) and/or arylsiloxane (preferably methylphenyl siloxane or diphenylsiloxane) repeating units, and at least one modified dialkylsiloxane or modified arylsiloxane repeating unit wherein one alkyl or aryl group of said repeating unit is replaced with a hydrophilic side group, and are such that the total number of repeating units (a) and repeating units (b) is at least 5 and less than 1,000. In one specific embodiment of the present invention, the repeating units (b) represent from 1% to 30% of the total number of repeating units (a) and repeating units (b). The repeating units (a) form part of what is hereinafter called a "silicone precursor". The repeating units (a) may be of a single type (e.g. preferably dimethylsiloxane), or mixed types (e.g. dimethylsiloxane and diphenyl-siloxane) in any proportions. In the latter case, they may be arranged randomly in the polymer chain, or they may be arranged in the form of block copolymers, for instance polydiphenylsiloxane-polydimethylsiloxane-polydiphenyl-siloxane tri-block copolymers.

In a broader embodiment of the present invention rubber or elastomeric polymer materials taking up more than 5% by weight of water and at most 500% by weight of water after immersion in demineralized water at room temperature for a sufficient time (such as 5 days or more) to reach saturation, and being useful as parts or components of the above-referred medical and non-medical devices (first and second objects of the invention) may comprise:

repeating units from one or more hydrophobic organic monomers, and repeating units from one or more monomers (a) being modified with one or more hydrophilic side groups. See comment of side group and main chain and that hydrophilic molecule with two or more reactive groups, depending on which crosslink chemistry is used, will result in polymers where the hydrophilic molecules or not side groups but become part of the main chain of the polymer matrix.

Said polymer material may be any rubbery or elastomeric polymer material, e.g. one wherein said hydrophobic organic monomer (a) is selected from the group consisting of butadiene, isoprene, dialkylsiloxanes, diarylsiloxanes, fluorinated siloxanes, acrylic acid alkyl esters (wherein the alkyl group has from 1 to 8 carbon atoms), acrylonitrile, chloroprene, fluorinated ethylene, mixtures of ethylene and vinyl acetate, mixtures of ethylene and one or more acrylic acid alkyl esters (wherein the alkyl group has from 1 to 8 carbon atoms), and mixtures of ethylene with propylene and a diene.

In one specific embodiment of the present invention, the rubbery or elastomeric polymer material may take up more than 10% by weight of water, more preferably more than 20% by weight of water, most preferably more than 40% by weight of water, and up to 200%, or up to 250% by weight, or up to 120% by weight of water after immersion in demineralized water at room temperature for a sufficient time (such as, but not limited to, 5 days or more) to reach saturation.

In one embodiment of the present invention, the rubbery polymer material may be one wherein said hydrophobic organic monomer (a) is a dialkylsiloxane or a diarylsiloxane, and wherein the total number of repeating units (a) and repeating units (b) is at least 5 and less than 1,000.

In one embodiment of the present invention, said polymer material may be one wherein said hydrophilic side groups are ionic side groups such as, but not limited to, $C_3$-$C_{28}$ alkylsulfonate groups in association with a cation. Said cation may be a monovalent cation selected from the group consisting of ammonium and alkali metal (Li, Na, K) cations, or a divalent cation selected from the group consisting of alkaline-earth metal cations (Ca, Mg). A detailed description of these ionic side groups and associated ions is given below.

In one embodiment of the present invention, said rubbery or elastomeric polymer material may be one wherein the repeating units (b) represent from 1% to 30%, for instance from 2% to 25%, or from 3% to 20%, or from 5% to 15%, of the total number of repeating units (a) and repeating units (b). The proportion of repeating units (b) present in the rubbery or elastomeric polymer material may be appropriately selected by the skilled person depending upon parameters such as, but not limited to, the type of repeating units (b), the desired level and kinetics of water uptake, and the kind of medical device, health care device or non-medical device comprising said rubbery or elastomeric polymer material.

In one embodiment of the present invention, said rubbery or elastomeric polymer material may further comprise a detectable amount of a ligating compound or ligand. Said ligating compound or ligand may be a cyclic compound such as, but not limited to, a crown ether, a cryptand or a calixerene. The amount of ligating compound or ligand present in the rubbery or elastomeric polymer material may depend upon parameters such as, but not limited to, the type and proportion of repeating units (b), the type of ligating compound or ligand, and polymerization conditions.

In one embodiment of the present invention, a polymerizable composition suitable for producing a rubbery or elastomeric polymer material such as recited herein-above, may comprise:

one or more hydrophobic organic monomers or pre-polymers, one or more hydrophilic monomers capable of modifying said hydrophobic organic monomers or pre-polymers (a) especially under liquid phase polymerization conditions, being for instance a $C_3$-$C_{28}$ alkenyl sulfonate in association with a cation, and a ligating compound or a solvent in an amount sufficient to increase solubility or miscibility of said hydrophilic monomers (b) in said hydro-phobic organic monomers or pre-polymers (a) under polymerization conditions.

The hydrophobic organic monomers or pre-polymers (a) may be biocompatible in view of medicinal applications, such as drug delivery, of the resulting polymer. This feature is especially relevant to medical devices of this invention such as, but not limited to, transdermal patches (e.g. a nicotine patch wherein the drug is slowly released from the rubbery material) or delivery devices for non-charged polar drugs (e.g. propranolol) and for positively or negatively charged drugs.

In one specific embodiment of the present invention, the hydrophilic side group of said repeating units (b) may be an alkylsulfonate group having from 3 to 28 (preferably 10 to 18, more preferably 12 to 16) carbon atoms in association with a cation. Said cation may be a monovalent cation selected from the group consisting of ammonium and alkali metal cations (such as, but not limited to, the cations of Li, Na, or K). Said cation may also be a divalent cation selected from the group consisting of alkaline-earth metal cations (such as the cations of Ca or Mg).

Other hydrophilic side groups can also comprise at least one moiety from ionic groups such as sulfate ($-OSO_3^-$), phosphate ($-OPO_3^{2-}$), phosponate ($-PO_3^{2-}$), carboxylate ($-CO_2^-$), ammonium ($NR_1R_2R_3R_4^+$), or phosphonium ($PR_1R_2R_3R_4^+$) or combinations of these groups like in betaine ($R_1R_2R_3N^+-CR_4R_5-CO_2^-$) or sulfobetaine ($R_1R_2R_3N^+-CR_4R_5-SO_3^-$). It can also contain non ionic hydrophilic groups like alcohol groups such as hydroxy ($-OH$), glycols ($-OCH_2CH_2OH$), or sugar derivates, ethers such as glycol ether ($-(OCH_2CH_2-)_nOR$), amines ($-NR_1R_2$), amides ($-CONR_1R_2$), phosphine oxide ($-POR_1R_2$), aldehydes ($-CHO$) or esters ($-COOR$). Preferred counter ions comprise the before mentioned ammonium, alkali, earth alkali ions, $H^+$ or mixtures and for the positive hydrophilic side chains the preferred counter ions are the halogenides ($F^-$, $Cl^-$, $Br^-$, $I^-$), hydroxide ($OH^-$), acetate ($CH_3COO^-$), sulfite ($SO_3^{2-}$), sulfate ($SO_4^{2-}$), nitrite ($NO_2^-$), nitrate ($NO_3^-$), phosphate ($PO_4^{3-}$), perchlorate ($ClO_4^-$) or tetrafluorborate ($BF_4^-$) or mixture thereof.

In another specific embodiment of the present invention, the hydrophilic side group of said repeating units (b) may be derived from a hydrophilic polymer selected from the group consisting of polyvinylpyrrolidones (usually with a number average molecular weight from 20,000 to 400,000), poly (hydroxyethyl methacrylates), poly-ethylene glycols (usually with a number average molecular weight from 200 to 10,000), polyvinyl alcohols (usually with a number average molecular weight from 10,000 to 150,000), polyacrylamides, alkali metal poly(meth)acrylates (such as, but not limited to, sodium polyacrylate, potassium polyacrylate, sodium polymethacrylate, potassium polymethacrylate), and mixtures thereof.

In one specific embodiment of the present invention, the polymer material may be a (partially) hydrophilic silicone-based rubber material wherein the molar ratio of the repeating units (a) to the repeating units (b) is at least 4.5, preferably at least 7, more preferably at least 9, most preferably at least 13. In one embodiment of the present invention, the polymer material may be a (partially) hydrophilic silicone-based rubber material wherein the molar ratio of the repeating units (a) to the repeating units (b) is at most 90, preferably at most preferably 40, most preferably at most 25.

In one specific embodiment of the present invention, the (partially) hydrophilic silicone-based rubber material may be a mixture of hydrophilic silicone rubber material and the hydrophilic molecule.

In one embodiment of the present invention, the polymer material may be a (partially) hydrophilic silicone-based rubber material further comprising residual traces or detectable amounts of a ligating compound or ligand that may be used during the process for its preparation. For instance when said hydrophilic side group is an alkylsulfonate having from 3 to 28 (preferably 10 to 18, more preferably 12 to 16) carbon atoms in association with a cation, said compound may be a cyclic ligand such as, but not limited to, a crown ether, a cryptand or a calixarene. Although there are effective procedures for removing a ligand such as a crown ether or a cryptand from a hydrophilic silicone-based rubber material of this invention, such as heating under vacuum, however it may be unnecessary to completely remove said ligand and residual but still detectable traces of the ligand may be admissible for medicinal applications. Methods for detecting and quantifying the presence of ligating compounds, such as crown ethers or cryptands, in a polymer material such as a (partially) hydrophilic silicone-based rubber material of the present invention are well known to the person skilled in the art.

In further embodiments of the present invention are provided processes for making silicone-based rubber materials described herein. In one embodiment of the present invention, a first process for preparing a hydrophilic silicone-based rubber material comprises the steps of:
(a) providing a silicone precursor and one or more hydrophilic monomers (preferably a vinyl-terminated hydrophilic monomer or other reactive groups which participate in the cross-linking reaction or polymers; and
(b) polymerizing said silicone precursor in the presence of said hydrophilic monomers or polymers, until obtaining a hydrophilic silicone-based rubber material which takes up more than 5% by weight (preferably more than 10% by weight, more preferably more than 15% by weight, most preferably more than 20% by weight) of water and at most 500% by weight (or at most 250% by weight, or up to 120% by weight), of water after immersion in demineralized water at room temperature for a sufficient time such as 5 days or more to reach saturation.

In another embodiment of the present invention, a second process for preparing a hydrophilic silicone-based rubber material comprises the steps of:
(a) providing a silicone precursor and one or more hydrophilic ionic monomers (preferably a vinyl-terminated hydrophilic ionic monomer or other reactive groups which participate in the cross-linking reaction) or polymers;
(b) polymerizing said silicone precursor in the presence of said hydrophilic ionic monomers or polymers and in the further presence of a ligating compound or solvent.

In another embodiment of the present invention, a third process for preparing a hydrophilic silicone-based rubber material comprises the steps of:
(a) providing a silicone precursor having Si—O repeating units, wherein the number of Si—O repeating units in said silicone precursor is at least 5 and less than 1000,
(b) providing one or more hydrophilic monomers (preferably a vinyl-terminated hydrophilic monomer) or polymers; and
(c) polymerizing said silicone precursor in the presence of said hydrophilic monomers or polymers.

In one embodiment of these processes, said silicone precursor may react with said hydrophilic monomers (preferably a vinyl-terminated hydrophilic monomer) or polymers. In particular said reaction may be via addition of a vinyl group onto a silicon-hydrogen bond. In one embodiment of the processes, said silicone precursor bears reactive Si—H groups with a spacer group between said reactive Si—H groups, which preferably comprises at least 5 and less than 1,000 silicon atoms interspersed with oxygen atoms. In the case of a peroxide catalyzed cross-linking method, the reaction is the polymerization of only vinyl bearing silicone and vinyl bearing hydrophilic molecules.

In another embodiment of these processes, said hydrophilic monomer may be an alpha-olefin or alkenyl sulfonate having 3 to 28 (preferably 10 to 18, e.g. 12 to 16) carbon atoms in association with a cation. Said cation may be a monovalent cation selected from the group consisting of ammonium and alkali metal cations (such as, but not limited to, the cations of Li, Na, or K). Said cation may also be a divalent cation selected from the group consisting of alkaline-earth metal cations (such as the cations of Ca or Mg). Other hydrophilic side groups can also comprise at least one moiety from ionic groups such as sulfate ($—OSO_3^-$), phosphate ($—OPO_3^{2-}$), phosponate ($—PO_3^{2-}$), carboxylate ($—CO_2^-$), ammonium ($NR_1R_2R_3R_4^+$), or phosphonium ($PR_1R_2R_3R_4^+$) or combinations of these groups like in betaine ($R_1R_2R_3N^+—CR_4R_5—CO_2$) or sulfobetaine ($R_1R_2R_3N^+—CR_4R_5—SO_3^-$). It can also contain non ionic hydrophilic groups like alcohol groups such as hydroxy ($—OH$), glycols ($—OCH_2CH_2OH$), or sugar derivates, ethers such as glycol ether ($—(OCH_2CH_2—)_nOR$), amines ($—NR_1R_2$), amides ($—CONR_1R_2$), phosphine oxide ($—POR_1R_2$), aldehydes ($—CHO$) or esters ($—COOR$). Preferred counter ions comprise the before mentioned ammonium, alkali, earth alkali ions, $H^+$ or mixtures and for the positive hydrophilic side chains the preferred counter ions are the halogenides ($F^-$, $Cl^-$, $Br^-$, $I^-$), hydroxide ($OH^-$), acetate ($CH_3COO^-$), sulfite ($SO_3^{2-}$), sulfate ($SO_4^{2-}$), nitrite ($NO_2^-$), nitrate ($NO_3^-$), phosphate ($PO_4^{3-}$), perchlorate ($ClO_4^-$) or tetrafluorborate ($BE_4^-$) or mixtures thereof.

In one embodiment of these processes, said hydrophilic polymer may be selected from the group consisting of polyvinylpyrrolidones (usually with a number average molecular weight from 20,000 to 400,000), poly(hydroxyethyl methacrylates), polyethylene glycols (usually with a number average molecular weight from 200 to 10,000), polyvinyl alcohols (usually with a number average molecular weight from 10,000 to 150,000), polyacrylamides, alkali metal poly(meth)acrylates (such as, but not limited to, sodium polyacrylate, potassium polyacrylate, sodium polymethacrylate, potassium polymethacrylate), and mixtures thereof.

In one embodiment of these processes, said silicone precursor reacts with said hydrophilic monomer or polymer in the presence of a ligating compound or a solvent. The ligating compound may be a cyclic ligating compound such as, but not limited to, a crown ether, a cryptand or a calixarene, for instance a crown ether capable of dissolving the cation associated with the alpha-olefin or alkenyl sulfonate having 3 to 28 (preferably 10 to 18, more preferably 12 to 16) carbon atoms. A suitable crown ether may depend upon the atomic size of the cation. In one embodiment, the cation is a lithium ion and the crown ether is a 12-crown-4 crown ether. In one embodiment, the cation is a sodium ion and the crown ether is a 15-crown-5 crown ether. In another embodiment, the cation is a potassium ion and the crown ether is a 18-crown-6 crown ether.

In place of a ligating compound, a solvent may be used to assist dissolution of the alkenyl sulfonate into the siloxane precursor. In one embodiment, the solvent has a very low boiling point. In another embodiment, the solvent may be a ketone (such as, but not limited to, acetone), another polar solvent (such as, but not limited to, chloroform), a low boiling alcohol (such as, but not limited to, ethanol) or a mixture of said low boiling alcohol with water.

In another embodiment of the present invention, the solvent may have a higher boiling point, e.g. between 100° C. and 300° C., in order to provide a more stable mixture during the production process. This higher boiling solvent can be an alcohol (such as, but not limited to, isopropanol, hexanol or decylalcohol), an ether (such as, but not limited to, an ethylene- or propylene-glycol ether or di- and trimers of ethylene or propylene glycol), a ketone (such as, but not limited to methylethylketone, methyl-propylketone or cyclohexanone), a chlorinated solvent such as, but not limited to, trichloroethylene, tetrachloroethylene or (di)chlorobenzene or any another polar solvent.

In one embodiment of each of these processes, the resulting hydrophilic silicone-based rubber material comprises at least one material represented by the following structural formula:

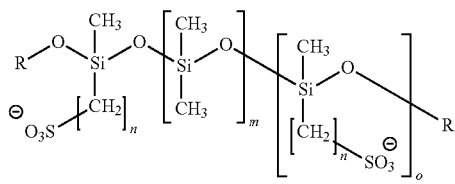

R = Si(CH₃)₃ or H wherein n is from 3 to 28 (preferably 10 to 18, more preferably 12 to 16) and wherein the total number (m+o+1) of repeating units is at least 5 and less than 1,000, with n and o being integers independently selected from each other and preferably being at least 6.

In one embodiment of the present invention, the hydrophilic silicone-based rubber material comprises at least one material represented by the above structural formula, wherein the molar ratio m/o is at least 4.5, preferably at least 7, more preferably at least 9, most preferably at least 13. In one embodiment of the present invention, the hydrophilic silicone-based rubber material comprises at least one material represented by the above structural formula, wherein the molar ratio m/o is at most 90, preferably at most preferably 40, most preferably at most 25.

In one specific embodiment of the present invention, a hydrophilic silicone material comprises a silicone precursor material, a sodium alpha-olefin sulfonate, and a crown ether mixing mediator that facilitates mixing of the sodium alpha-olefin sulfonate with the silicone precursor material. The silicone precursor material may be a commercial silicone elastomer material such as, but not limited to, Elastosil LR 3004/40 from Wacker Silicones (Germany). The sodium alpha-olefin sulfonate is also a commercially available product, or may be produced according to methods well known in the art. The crown ether may be a 15-crown-5 ether.

In one embodiment of the present invention, the hydrophilic silicone material includes from 40 to 98.5% by weight of the silicone precursor material, from 1 to 30% by weight of the sodium alpha-olefin sulfonate, and up to 30% by weight of the mixing mediator, and it takes up from 1 to 85% by weight of water after immersion in demineralized water for 5 days at room temperature.

In a further embodiment of the present invention, a method for manufacturing a hydrophilic silicone material includes the steps of:

mixing a sodium alpha-olefin sulfonate with a component of a silicone precursor material and with a crown ether or solvent mixing mediator, adding a silicone precursor B component, mixing again, and obtaining a hydrophilic silicone mixture.

The method for manufacturing a hydrophilic silicone material includes standard production techniques such as steps of casting or molding the hydrophilic silicone mixture, curing the hydrophilic silicone mixture, and obtaining the hydrophilic silicone material. The method further includes the steps of: mixing the sodium alpha-olefin sulfonate with the silicone precursor material and with the mixing mediator. Also mixing of hydrophilic silicone and sodium alpha-olefin sulfonate without mediator is possible. One embodiment of the method includes the steps of providing a commercial sodium alpha-olefin sulfonate, providing a commercial silicone elastomer as the silicone precursor material, and providing a 15-crown-5 ether as the mixing mediator. The method for manufacturing a hydrophilic silicone material includes further the step of performing the mixing at a temperature such as room temperature.

In a more general aspect, the present invention provides a process for preparing rubbery or elastomeric polymer materials, either in bulk or as coatings or sheets or fibers, useful as parts or components of the above-referred medical and non-medical devices (first and second objects of the invention), comprising the steps of:

providing one or more hydrophobic organic monomers, providing one or more hydrophilic monomers or polymers, and polymerizing said hydrophobic organic monomers in the presence of said hydrophilic monomers or polymers until obtaining a rubbery or elastomeric polymer material wherein repeating units from the one or more hydrophobic organic monomers are modified with hydrophilic groups from said one or more hydrophilic monomers or polymers, said rubbery or elastomeric polymer material taking up more than 5% by weight of water and at most 500% by weight of water after immersion in demineralized water at room temperature for a sufficient time (such as, but not limited to, 5 days or more) to reach saturation.

In a further embodiment of this general method, polymerization occurs in the presence of a ligating compound or a solvent for said hydrophilic monomer or polymer. In one embodiment of the present invention said ligating compound is a crown ether, a cryptand or a calixarene such as described herein-above. In one embodiment of the present invention, the solvent has a very low boiling point. In another embodiment of the present invention, the solvent may be a ketone (such as, but not limited to, acetone), another polar solvent (such as, but not limited to, chloroform), a low boiling alcohol (such as, but not limited to, ethanol) or a mixture of said low boiling alcohol with water. In another embodiment of the present invention, the solvent may have a higher boiling point, e.g. between 100° C. and 300° C., in order to provide a more stable mixture during the production process. This higher boiling solvent can be an alcohol (such as, but not limited to, isopropanol, hexanol or decylalcohol), an ether (such as, but not limited to, an ethylene- or propylene-glycol ether or di- and trimers of ethylene or propylene glycol), a ketone (such as, but not limited to methylethylketone, methyl-propylketone or cyclohexanone), a chlorinated solvent such as, but not limited to, trichloroethylene, tetrachloroethylene or (di)chlorobenzene or any another polar solvent.

When the rubbery or elastomeric polymer material for use in the manufacture of a medical, health care or non-medical device of this invention is in the form of a silicone-based foam, a suitable foaming composition is required. This foaming composition may be one as recited in the third object of the present invention herein-above. Exemplary details of such foaming compositions are provided below.

A hydroxyl source is necessary to properly blow the foamable composition and may be in the form of one or more hydroxylated components. The source of hydroxyl may be selected from the group consisting of water, organic alcohols, silanols and mixtures thereof. Suitable silanols include any hydroxylated organosiloxane having an average of 1 to 2.5 silicon-bonded hydroxyl radicals per molecule. The silanols may be monomers, homopolymers, copolymers or mixtures thereof. Examples of suitable silanols include, but are not limited to, hydroxyl end-capped polydimethylsiloxane, hydroxyl end-capped dimethylsiloxane/phenylmethylsiloxane copolymers, hydroxyl end-capped polymethyl-3,3,3-trifluoropropylsiloxane and diphenylmethylsilanol.

Organic alcohols suitable for use herein may be monoalcohols or polyols, preferably having from 1 to 12 carbon atoms. Suitable organic alcohols include, but are not limited to, ethanol, propanol, butanol, lauryl alcohol, octyl alcohol, ethylene glycol, and benzyl alcohol. The hydroxyl source may react with hydrogen of the hydrophobic siloxane or silicone precursor to produce hydrogen gas. Water will react with hydrogen of the hydrophobic siloxane or silicone precursor to produce a hydroxyl function which can further react to produce additional gas and a cross-link site. Thus, where water is the hydroxyl source, additional gas will be generated as a benefit, but gassing after cure may occur. Silanol, due to good solubility in the composition, produces gas immediately but may lead to problems of premature gelation. Organic alcohols do not as easily react with the hydrogen function and thus are generally used in combination with silanol or water Depending on the hydroxyl source used, there should be from 0.02 to 5 hydroxyl groups from the hydroxyl source for each silicone-bonded hydrogen atom in the hydrophobic siloxane or silicone precursor. Alternatively the hydroxylated component(s) should constitute not more than 2% by weight of the foamable composition.

Suitable platinum catalysts are preferably soluble in the other ingredients of the foaming composition. They can be selected from the group of compounds having the formulae $(PtCl_2.Olefin)_2$ and $H(PtCl_3.Olefin)$, as described in U.S. Pat. No. 3,159,601. The olefin shown in these formulae is preferably an alkene having from 2 to 8 carbon atoms, a cycloalkene having from 5 to 7 carbon atoms, or styrene. Specific suitable olefins include, but are not limited to, ethylene, propylene, butene, octene, cyclopentene, cyclohexene, and cycloheptene, A further suitable platinum catalyst is the platinum chloride cyclopropane complex $(PtCl_2C_3H_6)_2$ described in U.S. Pat. No. 3,159,662, or a complex formed from chloroplatinic acid with up to 2 moles per gram of platinum of a ligand selected from the group consisting of alcohols, ethers, aldehydes and mixtures thereof as described in U.S. Pat. No. 3,220,972.

Another suitable platinum catalyst (see U.S. Pat. No. 3,775,452) may be formed by reacting chloroplatinic acid containing 4 moles of water of hydration with tetramethyltetravinylcyclosiloxane in the presence of sodium bicarbonate in an ethanol solution.

Platinum catalysts may be deposited on carriers such as silica gel or powdered charcoal.

An amino compound optionally suitable and effective to lower silicone foam density has the formula $NR_3$ wherein each R is independently selected from the group consisting of hydrogen, hydroxyl, $C_{1-18}$ alkyl, $C_{3-10}$ cycloalkyl, aryl (e.g. phenyl), and silyl, provided that at most one R may be hydroxy and provided that not all three R are hydrogen. Suitable amino compounds include, but are not limited to, hydroxylamines (e.g. diethyl hydroxyl amine), primary, secondary and tertiary amines, and silylamines, for example tetramethylpiperidine, piperidine, N-methylmorpholine, N,N-dimethyl-ethylenediamine, N-methylipiperidine, N-hexylamine, tributylamine, dibutylamine, cyclohexylamine, di-n-hexylamine, triethylamine, benzylamine, dipropylamine, N-ethyl-phenylamine, tetramethylguanidine, hexamethyldisilazane and N-methylmorpholine. Preferably the amino compound should be soluble in the foamable composition.

Hydrophobic organic monomers suitable for the foaming compositions of the invention include, but are not limited to, polysiloxanes having not less than 5 alkylhydrogensiloxane units per molecule, polysiloxanes having not less than two silicon-bonded hydroxyl groups per molecule, fluorinated polyorganosiloxanes. Monomers or polymers with hydrophilic side groups suitable for the foaming compositions of the invention are as described previously with respect to the bulk and coating hydrophilic silicone materials.

Preferably, the foaming composition of the invention is provided in the form of two or more parts for admixture just prior to forming said composition, and each of said parts has a similar viscosity as the other one at 25° C.

Reactions of components of the foaming compositions to generate hydrogen gas and to cure the mass through chain extension and crosslinking within the desired time span are dependent on presence of appropriate proportions of these components, especially the alkylhydrogen polysiloxane. Preferably this polysiloxane should have from 0.5% to 2.5% by weight of silicon-bonded hydrogen atoms.

These components are preferably liquids with appropriate functionality and chain length to achieve the target viscosity required for the composition, the amount of hydrogen evolution and the degree of chain extension and crosslinking required during curing of the composition. Suitable polysiloxanes having silicon-bonded hydroxyl groups are preferably silanol terminated polydiorganosiloxanes.

One may optionally include in the foaming composition appropriate amounts of higher functional materials as crosslinking agents. Suitable crosslinking agents include materials having three or more functional, e.g. hydroxyl, groups per molecule. Preferred crosslinking agents include an alkoxysilane and/or a condensation product thereof capable of combining with three or more hydroxy polysiloxane molecules with release of the corresponding alcohol, e.g. methyl trimethoxysilane, n-propylortho-silicate or ethyl polysilicate.

The foaming compositions of the present invention may also include up to 10 percent, based on the weight of the hydrophobic siloxane, of $GSiO_{3/2}$ units wherein G is a residue obtained by removing the hydrogen atom from a hydroxyl group of a linear organic polymer selected from the group consisting of homopolymers of ethylenically unsaturated alcohols, copolymers of these alcohols with ethylenically unsaturated hydrocarbons, polyethers and polyoxyalkylene glycols, wherein said organic polymer contains an average of at least one terminal hydroxyl group per molecule, as described in European Patent No. 179.598.

Within the above definitions of various embodiments of the foaming compositions of the present invention, one may obtain rubbery or elastomeric silicone materials being in the form of a foam with a foam density from 60 to 300 kg/m$^3$. For instance, high density foams from 150 to 300 kg/m$^3$, or low density foams from 60 to 150 kg/m$^3$.

In a still further embodiment of the present invention, the hydrophilic silicone material is used as a component of a system in combination with a hydrophobic material such as, but not limited to, a hydrophobic silicone base material or a hydrophobic natural rubber material. At least a part of the hydrophilic material may be in contact with a moist surface while the hydrophobic base material provides mechanical and dynamical stability of the system. The hydrophilic material allows for uptake of moisture and diffusion of moisture away from the moist surface. The moist surface may be the skin of a human being. In one embodiment of the invention, the hydrophobic base material forms a base layer and the hydrophilic material forms a top layer placed above the base layer. In another embodiment of the present invention, the hydrophilic material is mixed into the hydrophobic base material to form a composite mixture. In a further embodiment, a layer of hydrophobic base material is formed at an outside of the composite mixture, the layer is perforated forming apertures, and the apertures connect the hydrophilic material with the moist surface. In still another embodiment of the invention, the hydrophobic base material includes a plurality of holes positioned at an interface of the hydrophobic base material with the moist surface, the holes are filled with the hydrophilic material, and the hydrophilic material is in contact with the moist surface.

The medical or health care device of the present invention may be selected from the group consisting of tight seals for adjusting to a part of the human face, nasal plugs, ear plugs, sterile bandages, medical cotton, absorbent pads, catheters, balloons, medical tubings, prosthetic implants, orthotic devices, orthodontic devices, medical and surgical wipes, bed sore protection devices, transdermal patches, delivery devices for non-charged polar drugs and positively or negatively charged drugs, anti-scarring plasters, body contact bands, hair care products, and biocompatible devices for medical diagnosis or treatment. Each of these embodiments is detailed below.

The medical or health care device of the present invention may be a tight seal for adjusting to a part of the human face, such as a nasal plug or an ear plug, comprising, e.g. made from a rubbery or elastomeric silicone foam such as described hereinbefore. Its hydrophilic property makes it more skin compatible than standard materials known in the art, and they can be used without any irritation for several hours. The diameter of the foam plug may be for instance around 10 mm. The plugs may be squeezed between the fingers and inserted in the nasal or ear cavity where they will expand and give a perfect fit. In a further embodiment of this invention, comfortable ear plugs may be made by applying the hydrophilic rubbery or elastomeric polymer material, e.g. the hydrophilic silicone as a coating onto a standard non-hydrophilic part or component of the ear plug and enable, in contact with skin or mucosa, improved moisture uptake.

In another embodiment, the medical or health care device of the present invention may be a catheter such as, but not limited to, a catheter for interventional procedures. In this invention hydrophilic silicones are used for catheters e.g. for cardiac and other interventional procedures. They a better gliding behavior than standard silicone catheters known in the art. Furthermore, a hydrophilic silicone may be applied either as a bulk material or as a coating on an urinary catheter, thus taking up body fluids from the mucosa and reducing mineral encrustation of the urinary catheter.

In another embodiment, the medical or healthcare device of the present invention may be a prosthetic implant such as, but not limited to, for breast, nose, limb, or ear.

In another embodiment, the medical or health care device of the present invention may be a long term sterile skin coating. For instance an adhesive bandage made of a hydrophilic silicone rubber of this invention keeps the skin highly moisturized. After one day its water holding capacity is completely saturated and stabilizes the high humidity level. This high humidity level is necessary to minimize scar formation of a recent wound or to minimize the appearance of old wound scars. This high humidity situation is prone to bacterial growth which is however stopped by the hydrophilic side groups in the rubber when said side groups are alkylsulfonate groups in association with a cation. The bandage may be made in different shapes to cover the different forms of wounds or old scars. It may have a rim with an adhesive to keep the plaster on its place and to seal it. Its thickness may be less than 1 mm to keep it very flexible and comfortable to wear.

In another embodiment, the medical or health care device of the present invention may be a delivery device for a non charged polar drugs, such as propranolol (a non selective beta blocker), which can be dissolved in the hydrophilic rubbery or elastomeric polymer (e.g.) material. It may also be a drug delivery device wherein the hydrophilic rubber (e.g. silicone) material of this invention is used to act as an ion exchanger to exchange its cation (e.g. sodium ions) for positively charged drugs. An example is a transdermal nicotine patch, wherein the drug is slowly released from the rubber material. This is not limited to only drug delivery where the drug is positively charged, but using positive charged side group also negatively charged drugs can be implemented.

In another embodiment, the medical or health care device of the present invention may be a band adapted to be applied to the wrist or another body part of a human for wearing sensors for e.g. vital sign monitoring.

In another embodiment, the medical or health care device of the present invention may be a medical grade silicone based product for hair care with improved adhesion.

The non-medical device of this invention may be selected, among others, from the group consisting of external and in-ear head sets, ear clips, nose and/or ear pieces of glasses, handles, textile and non-textile parts of shoes, building elements made of metal or plastic, parts (preferably underwater parts) of boats, printing stamps, clothing textiles, cosmetic compositions, printing inks, toner compositions, paint or coating compositions, surfactant compositions, antifoaming agents, rolling oil formulations (e.g. for metal drawing or stamping), wafer bonding agents (e.g. for semiconductors), anti-statics (e.g. for fiber processing), developers for lithographic plates, artificial sponges (e.g. nonwoven), anti-fog agents (for glass surfaces e.g. mirrors, eye-glasses, car windows), non-woven articles (e.g. for diapers), body contact belts and bands, seats, highly reflective products, sliding transportation systems, sliding sealing rings, and oil barriers in silicone rings. Each of these embodiments is detailed below.

In one embodiment, the non-medical device of the present invention may be a external head set or an in-ear head set (ear clip) for e.g. ear phones, audio systems or hearing aids wherein a hydrophilic silicone material is used in combination with a hydrophobic silicone base material. The hydrophilic silicone is applied in the ear phone head set in these parts that are in contact with the ear. The hydrophobic material can be for example used in the area outside of the ear. The hydrophilic silicones take the moisture up from the ear (e.g. during strong movements and sweating) and create in this way a more comfortable head set as well as a stronger fixed head set in the ear as with the hydrophobic silicones. For instance the skin contact material of the head set is build up from a layer of hydrophilic and hydrophobic silicones, where the hydrophilic silicone is in contact with the ear and the hydrophobic silicone underneath ensures stability.

In another embodiment, the non-medical device of the present invention may be one wherein improved long term stable grip is required. In the present invention, hydrophilic silicone rubber are used for stable grips by adsorbing sweat and keeps the rubber grip water free and non slippery. This may be a grip for a bike handle or a part of a wooden saw handle, a steering wheel or a joystick, which may be completely exchanged with the hydrophilic silicone rubber of this invention.

In another embodiment, the non-medical device of the present invention may be a textile or non-textile region in shoes. The hydrophilic silicones take moisture up and prevent wet feel due to sweating in the shoe. The hydrophilic silicone also prevents bacterial growth in shoes due to the hydrophilic side groups in the rubber (e.g. silicone) material when said side groups are alkylsulfonate groups in association with a cation.

In another embodiment, the non-medical device of the present invention may be a textile clothing, such as a sport cloth made from cotton. Coating the textile with the hydrophilic rubber (e.g. silicone) material enables moisture uptake and prevents cotton from feeling wet or damp after a prolonged period of time under sweating conditions.

In another embodiment, the non-medical device of the present invention may be a metal plastic plate (e.g. for an outdoor or indoor building element) on which a thin (e.g. not more than 1 mm thick) anti-condensation layer of a hydrophilic silicone rubber is applied. Its advantages are the good adhesion of metal, the low contact angle of water and most important stopping the growth of microorganisms such as, but not limited to, bacteria, fungi or algae due to the hydrophilic side groups in the rubber (e.g. silicone) material when said side groups are alkylsulfonate groups in association with a cation.

In another embodiment, the non-medical device of the present invention may be an underwater part of a boat, wherein a thin (i.e. not more than 1 mm thick), layer of hydrophilic rubber coating is applied to stop growth of waterborne organisms such as, but not limited to, barnacles and mussels due to the hydrophilic side groups in the rubber (e.g. silicone) material when said side groups are alkylsulfonate groups in association with a cation. This has the advantage of biodegradability and low toxicity compared to current tin toxins.

In another embodiment, the non-medical device of the present invention may be a human body contact region such as (optionally light weight and/or flame retardant) seats like chairs and armchairs as e.g. in airplanes, trains, buses, theaters, conference where preventing sweat and providing a comfortable seating experience is desirable.

In another embodiment, the non-medical device of the present invention may be a printing ink composition such as required for printing stents by tampon printing.

In another embodiment, the non-medical device of the present invention may be an oil barrier for a silicone ring as used in industrial or technical equipment.

BRIEF DESCRIPTION OF THE DRAWINGS

The present invention will now be described, by way of example, with reference to the accompanying drawings, in which.

Figure 1:
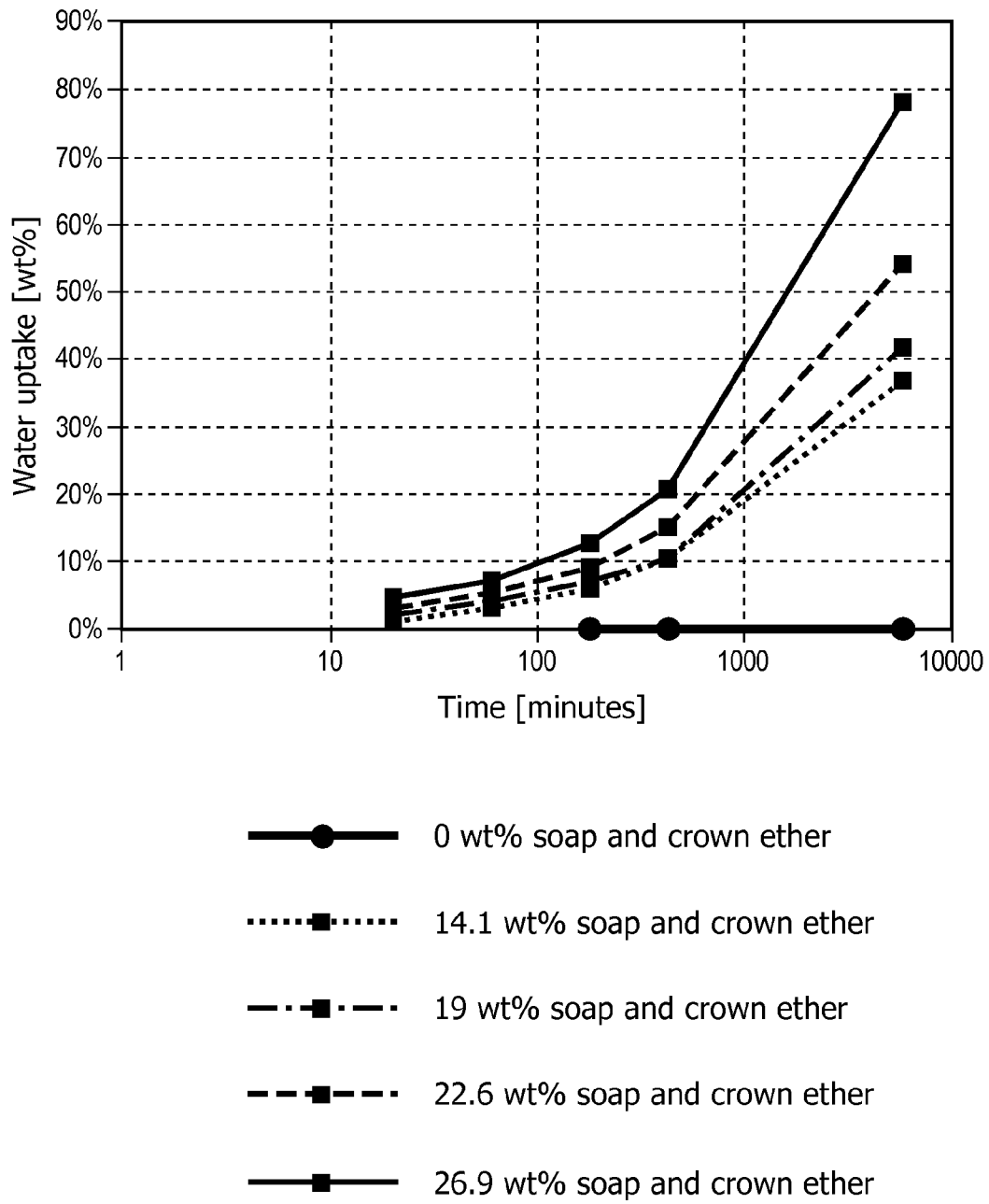
FIG. 1 and FIG. 2 show the water uptake of different hydrophilic silicone rubber materials (wherein the term "soap" is used as an abbreviation to designate sodium sulfonate groups) as a function of time, in comparison with a hydrophobic silicone rubber material without alkylsulfonate groups.

The exemplification set out herein illustrates exemplary embodiments of the invention, in one form, and such exemplification is not to be construed as limiting the scope of the invention in any manner.

DEFINITIONS

Hydrophobic materials are characterized by a water contact angle that is larger than that of hydrophilic materials. The larger the contact angle, the more hydrophobic is the material, the smaller the contact angle, the more hydrophilic is the material.

Examples of hydrophobic materials as used in the present invention are silicone rubbers, natural rubbers (latex), rubbers based on butadiene, isoprene, halogenated butadiene, perfluorinated rubbers (Viton) and acrylate rubbers, and mixtures thereof.

Hydrophilic materials are defined herein as polymers that allow the uptake and/or diffusion of water.

Examples of hydrophilic rubber materials include, but are not limited to, hydrophilic silicone rubbers with a crosslinking structure and/or a crosslinking density similar to that of hydrophobic silicone rubber materials. Hydrophilic silicones keep the silicone backbone structure but some of their hydrophobic methyl or phenyl groups are replaced with hydrophilic side groups.

DETAILED DESCRIPTION OF CERTAIN EMBODIMENTS

The present invention is described herein with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where an indefinite or definite article is used when referring to a singular noun e.g. "a" or "an", "the", this includes a plural of that noun unless something else is specifically stated.

The term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

In an embodiment in accordance with the present invention, a composition for the preparation of hydrophilic silicone materials suitable for moisture control, and being in bulk or in the form of coatings, is provided.

The synthesis of a suitable hydrophilic silicone according to this invention by two different cross-linking methods may be schematically described as follows:

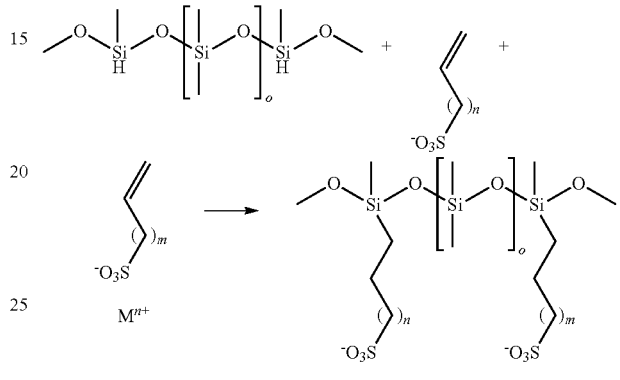

Platinum salt catalyzed crosslinking, and

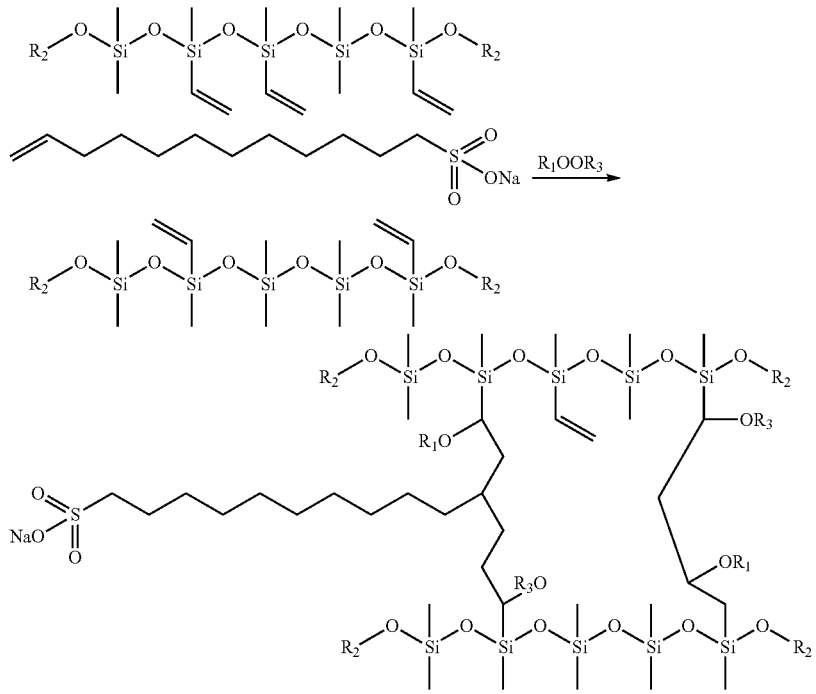

Peroxide Crosslinking

A silicone precursor bearing reactive Si—H or Si-vinyl groups reacts with a hydrophilic monomer such as an alpha-olefin sulfonate, wherein:

the values for n and m may range from 3 to 28, preferably from 10 to 18, and more preferably from 12 to 16, and wherein the value for o ranges from 5 to 1,000.

The olefin component may be strongly hydrophilic, because it may include a polar, negatively charged head group ($^-O_3S$) and a cation ($M^{n+}$) for charge balance. The mixing of the hydrophilic olefin component with the hydrophobic silicone precursor may be hampered by the difference in hydrophilicity. It may be particularly different to suspend the ion pair composed of the anionic head group and the cationic counter-ion in the hydrophobic matrix of the silicone precursor.

Adding a crown ether acting as a solubility- or mixing mediator may be highly effective and may allow for a simple, rapid, and highly reproducible synthesis of the desired hydrophilic silicone material. The choice of the most suitable crown ether may depend on the counter-cation used. For instance, the most efficient solubility mediator for dissolving the sodium ions in hydrophobic media is the 15-crown-5 ether, whereas the most suitable solubility mediator for dissolving potassium ions in hydrophobic media is the 18-crown-6 crown ether. The stabilization of metal ions in hydrophobic media by crown ethers, derivatives thereof, and related molecules, is well known in the art and has been described for instance in the following publications, the content of which is incorporated herein by reference:

H. J. Schneider et al., Chemical Society Reviews (2008) 37, 263-277;

Barannikov, Russian Journal of Coordination Chemistry (2002) 28, 153-162; and

J. W. Steed, Coordination Chemistry Reviews (2001) 215, 171-221; and references therein.

In an exemplary embodiment in accordance with the present invention, mixing a commercial silicone precursor material with a sodium alpha-olefin sulfonate may be facilitated by the addition of a crown ether mixing mediator. Sodium alpha-olefin sulfonates, such as sodium $C_{12-14}$ olefin sulfonate, sodium $C_{14-16}$ olefin sulfonate, sodium $C_{14-18}$ olefin sulfonate, or sodium $C_{16-18}$ olefin sulfonate, are mixtures of long chain sulfonate salts prepared by the sulfonation of alpha olefins. The numbers indicate the average length of the carbon chains of the alpha olefins. Other ligating compounds that may be suitable to form an inclusion complex with the chosen counter ion may be used as an alternative to crown ethers. An example of such compounds are calix[4]arenes as described in B. S. Creaven et al., Coordination Chemistry Reviews (2009) 253, pp. 893-962, the content of which is incorporated herein by reference.

The water-absorbing rubbery or elastomeric polymer material present in the medical, health care or non-medical device with high water-uptake capacity of the present invention may be in the form of a coating adapted for adhesion to a substrate. The substrate may be a piece of another polymer material or a piece of metal such as aluminum or steel or other metal alloys as used for instance in the building industry. The substrate may have any shape such as planar, curved, spherical or other, depending upon the type of device, as long as good adhesion is obtained.

The water-absorbing rubbery or elastomeric polymer material present in the medical, healthcare or non-medical device with high water-uptake capacity of the present invention, such as a textile, may be in the form of a fiber or fibrous material. Manufacture of silicone fibers such as used as fillers in polyester pillows, in particular hollow silicone fibers with a linear mass density from 1.5 to 25 deniers, are well known to the skilled person.

The following examples are purely illustrative of specific embodiments and should not be construed as limiting the scope of the present invention.

Example 1

The commercial silicone elastomer Elastosil LR 3004/40 (Wacker Silicones, Germany) was used as silicone precursor material. The silicone precursor material is a two component system that was mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups.

The sodium $C_{12-14}$ alkenyl sulfonate commercially available from The Chemistry Store.com (Cayce, S.C., United States) was first mixed with the A component of the silicone precursor material. This mixing process is generally energy-demanding as the two components are viscous and do not mix well. Heating to 120° C. may therefore be needed.

To facilitate mixing of the commercial sodium $C_{12-14}$ alkenyl sulfonate with the silicone precursor A component, a crown ether (15-crown-5) was used (10% w/w with respect to the total amount of components A and B) as a mixing mediator. After addition of the crown ether, mixing was found to be straight forward and easily accomplished at room temperature.

More specifically, the commercial sodium alpha-olefin sulfonate (2 g) was mixed with 15-crown-5 (2 g) and silicone precursor A component (10 g). Mixing was performed at room temperature (SpeedMixer™ DAC 150 FVZ-K, Hauschild, Germany, twice 2 minutes, 3300 rpm). Then silicone precursor B component (11.4 g) was added and the obtained composition was mixed again (same mixer, twice 2 minutes, 3300 rpm). The resulting silicone composition was thus comprised of 84% by weight of the commercial silicone precursor material, 8% by weight of a commercial sodium alpha-olefin sulfonate, and 8% wt of the mixing mediator 15-crown-S.

Material samples were prepared by casting the above mixture onto the surface of a glass substrate and curing (30 minutes, 130° C.) under reduced pressure (<10 mbar). After curing, the water uptake of the silicone material (sample A) was compared with that of two other materials:

a material sample that was made with 20% by weight of the sodium alpha-olefin sulfonate without crown ether (sample B), and a material sample that was made of the commercial silicone elastomer Elastosil 3004/40 according to the instructions of the manufacturer (sample C).

After immersion of all three samples in demineralized water for 5 days, the Elastosil 3004/40 (sample C) had taken up 0.3% by weight water, the new silicone material comprising the sodium alpha-olefin sulfonate and the crown ether mixing mediator (sample A) had taken up 43% by weight water, whereas the sample B comprising only the sodium alpha-olefin sulfonate but no 15-crown-5 mixing mediator, had taken up 40% by weight water.

Water uptake (weight %) as a function of time of different amounts of sodium $C_{12-14}$ alkenyl sulfonate with equal amounts of 15-crown-5 in Elastosil LR3004/40 along the route described herein are shown in FIG. 1.

In the following examples 2-5, the amount of commercial sodium $C_{12-14}$ alkenyl sulfonate added to the amount of silicone precursors A+B is given in percentage and calculated along weight sodium $C_{12-14}$ alkenyl sulfonate/weight silicone A+B*100. The values for the percentage silicone precursor A+B given in examples 2-5 are the values for 100%-amount sodium $C_{12-14}$ alkenyl sulfonate %.

Example 2

The commercial silicone elastomer Elastosil LR 3004/40 (Wacker Silicones, Germany) was used as silicone precursor material. The silicone precursor material is a two component system that was mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups.

The sodium alpha-olefin sulfonate RCH═CH$(CH_2)_n$SO$_3$Na (n=12-14) commercially available from The Chemistry Store.com (Cayce, S.C., United States) with a particle size above 400 µm was first mixed with the A component of the silicone precursor material. This mixing process is generally energy-demanding as the two components are viscous and do not mix well. Heating to 120° C. may therefore be needed.

To facilitate mixing of the commercial sodium alpha-olefin sulfonate with the silicone precursor A component, a crown ether (15-crown-5) acetone mixture was used as a mixing mediator. After addition of the crown ether and acetone mixing was found to be straight forward and easily accomplished at room temperature.

More specifically, the commercial sodium alpha-olefin sulfonate (12 g) was mixed in a first step with 15-crown-5 (7 g) and 7 g acetone. After this the silicone precursor A component (19 g) was added. Mixing was performed at room temperature (Speed Mixer™ DAC 150 FVZ-K, Hauschild, Germany, twice 2 minutes, 3300 rpm). The crown ether and acetone were removed in vacuum at 0.05 mbar, 90° C. Then silicone precursor B component (26.1 g) was added and the obtained composition was mixed again (same mixer, twice 2 minutes, 3300 rpm). The resulting silicone composition was thus comprised of 73.4% by weight of the commercial silicone precursor material, and 26.6% by weight of the commercial sodium alpha-olefin sulfonate.

Material samples were prepared by casting the above mixture onto the surface of a glass substrate and curing (30 minutes, 130° C.) under a nitrogen atmosphere.

Example 3

In a further example the commercial silicone elastomer Elastosil LR 3004/40 (Wacker Silicones, Germany) was used as silicone precursor material. The silicone precursor material is a two component system that was mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups.

A commercial sodium alpha-olefin sulfonate RCH═CH$(CH_2)_n$SO$_3$Na (n=12-14) from Stepan Company (Northfield, Ill., United States) was used. This very fine powder (particle sizes below 400 µm) was mixed with the A component of the silicone precursor material by speed mixing. More specifically, commercial sodium alpha-olefin sulfonate (12 g) was mixed with silicone precursor A component (19 g). Then silicone precursor B component (26.1 g) was added and the obtained composition was mixed. The resulting silicone composition was thus comprised of 73.4% by weight of the commercial silicone precursor material, and 26.6% by weight of a commercial sodium alpha-olefin sulfonate.

Material samples were prepared by pressure molding at 130° C.

Example 4

In a further example the commercial silicone elastomer Elastosil LR 3004/40 (Wacker Silicones, Germany) was used as silicone precursor material. The silicone precursor material is a two component system that was mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups.

A commercial sodium alpha-olefin sulfonate RCH═CH$(CH_2)_n$SO$_3$Na (n=12-14) from Stepan Company (Northfield, Ill., United States) was used. 12 g of this very fine powder (particle sizes below 400 µm) was mixed with 7 g ethanol. Then 19 g of the A component of the silicone precursor material added and mixing was carried out with a speed mixer. After mixing the ethanol was removed under vacuum at 60° C. Then silicone precursor B component (26.1 g) was added and the obtained composition was mixed. The resulting silicone composition was thus comprised of 73.4% by weight of the commercial silicone precursor material, and 26.6% by weight of a commercial sodium alpha-olefin sulfonate.

Material samples were prepared by pressure molding at 130° C.

Example 5

In a further example the commercial silicone elastomer Elastosil LR 3004/40 (Wacker Silicones, Germany) was used as silicone precursor material. The silicone precursor material is a two component system that was mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups.

A commercial sodium alpha-olefin sulfonate RCH═CH$(CH_2)_n$SO$_3$Na (n=12-14) from Stepan Company (Northfield, Ill., United States) was used. 12 g of this very fine powder (particle sizes below 400 µm) was mixed with 7 g of an ethanol water mixture (50/50% by volume). Then 19 g of the A component of the silicone precursor material added and mixing was carried out with a speed mixer. After mixing the ethanol was removed under vacuum at 90° C. Then silicone precursor B component (26.1 g) was added and the obtained composition was mixed. The resulting silicone composition was thus comprised of 73.4% by weight of the commercial silicone precursor material, and 26.6% by weight of a commercial sodium alpha-olefin sulfonate.

Figure 2:
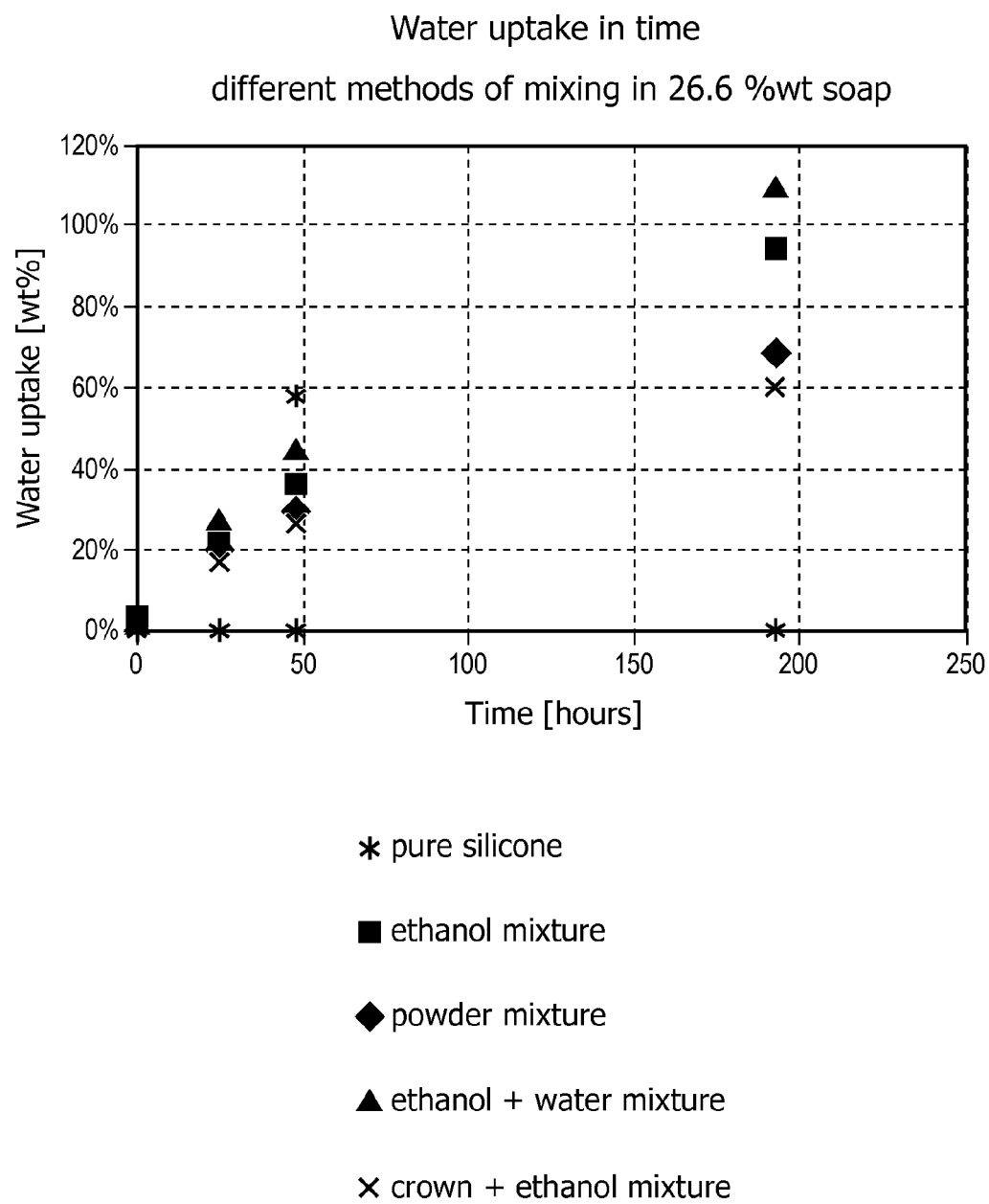

Material samples were prepared by pressure molding at 130° C. Water uptake (weight %) as a function of time of different mixing methods of sodium $C_{12-14}$ alkenyl sulfonate with Elastosil LR3004/40 along the above route described in examples 2-5 is given in FIG. 2.

Example 6

In a 2.5 liter jacketed glass reactor, a mixture of 55 g butylmethacrylate (BMA) (purity above 99%), 2200 g water of a conductivity of 18.2 MΩ·cm and 0.6 g of a commercial sodium alpha-olefin sulfonate RCH═CH(CH$_2$)nSO$_3$Na (n=12-14) from Stepan Company (Northfield, Ill., United States) are mixed and degassed under nitrogen while stirring at 500 rpm (using a double bladed stirrer). In order to reduce the chain length of the polymer, by controlling the micelle size of the BMA droplets in water, from 1 to 2% by weight of surfactant (e.g. sodium alpha-olefin sulfonate) is added to the monomer mixture. Then the reactor is put under nitrogen and the mixture is heated to 80° C. After addition of the initiator solution (for instance 1.6 g ammonium persulfate 98% in 50 g of water of a conductivity of 18.2 M□·cm) at 80° C., the stirring speed is reduced to 350 rpm. Polymerisation is carried out for at least 3 hours.

Example 7

In this example the commercial silicone elastomer Elastosil LR 3003/5 (commercially available from Wacker Silicones, Germany) was used as the silicone precursor material. The silicone precursor material is a two component system that was normally mixed in a 1:1 weight ratio of two components A and B. The A component consists of a silicone pre-polymer bearing reactive vinyl groups and a platinum catalyst. The B component consists of a silicone pre-polymer bearing reactive vinyl groups and a pre-polymer bearing Si—H groups. A commercial sodium alpha-olefin sulfonate RCH═CH(CH$_2$)$_n$SO$_3$Na (n=12-14) from Stepan Company (Northfield, Ill., United States) was used. 12 g of this very fine powder (particle sizes below 400 μm) was mixed with 7 g of an ethanol water mixture (50/50% by volume). Then 19 g of the A component of the silicone precursor material was added and mixed with a speed mixer. After mixing the ethanol and water were removed under vacuum at 60° C. until a small amount (±0.5 gram) of water was still present. Then silicone precursor B component (24.7 g) was added and the obtained composition was mixed. The commercial sodium alpha-olefin sulfonate added to the silicone precursors A+B, is thus amounting to 27.5 weight % of silicone precursor (A+B) weight ((weight sodium alpha-olefin sulfonate/weight silicone A+B)*100). The mixing ratio of this system for component A to B was 1 to 1.3. Material samples were prepared by pressure molding at 130° C. for 10 to 15 minutes at 711 psi.

While the invention has been described by reference to various specific embodiments, it should be understood that numerous changes may be made within the spirit and scope of the inventive concepts described herein. Accordingly, it is intended that the invention not be limited to the described embodiments, but will have full scope defined by the language of the following claims.

The invention claimed is:

1. An aqueous fluid absorbing, medical or health care device, comprising:
 a rubbery or elastomeric polymer material effective to take up more than 40% by weight and up to 500% by weight of water after immersion in demineralized water at room temperature for a sufficient time to reach saturation, of the formula I:

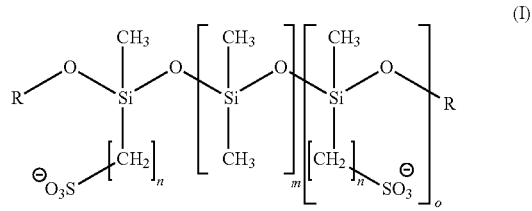

R = Si(CH$_3$)$_3$ or H (I)

wherein, R is Si(CH$_3$)$_3$ or hydrogen, n is from 3 to 28, and (m+o+1) is at least 5 and less than 1,000,
said polymer material, comprising:
 (a) repeating units from one or more hydrophobic organic monomers;
 (b) repeating units from the one or more monomers being modified with C$_{3-28}$ alkylsulfonate or alkenylsulfonate side groups in association with a cation selected from the group consisting of ammonium, Li, Na and K, Ca and Mg, and the repeating units (b) constituting from 1% to 30% of a total number of repeating units (a) and repeating units (b); and
 a detectable trace of a ligand selected from the group consisting of crown ether, cryptand and calixerene, wherein, said device is a medical or health care device selected from the group consisting of tight seals for adjusting to a part of the human face, nasal plugs, ear plugs, sterile bandages, medical cotton, absorbent pads, catheters, balloons, medical tubings, prosthetic implants, orthotic devices, orthodontic devices, medical and surgical wipes, bed sore protection devices, transdermal patches, delivery devices for non-charged polar drugs and positively or negatively charged drugs, anti-scarring plasters, body contact bands, hair care products, and biocompatible devices for medical diagnosis or treatment.

2. A medical device according to claim 1, wherein said rubbery or elastomeric polymer material is for contact with the skin or a mucosa of a human.

3. A device according to claim 1, wherein said rubbery or elastomeric polymer material is in the form of a sheet.

4. A device according to claim 1, wherein said rubbery or elastomeric polymer material is in the form of a foam.

5. A device according to claim 4, wherein the density of said foam is from 60 to 300 kg/m$^3$.

6. A device according to claim 1, wherein said rubbery or elastomeric polymer material is in the form of a coating adapted for adhesion to a substrate.

7. A device according to claim 1, wherein said rubbery or elastomeric polymer material is in the form of a fiber.

8. The device according to claim 1, wherein said rubbery or elastomeric polymer material is prepared by a method, comprising:
 mixing together silicone precursor, sodium C$_{3-28}$ alkylsulfonate or alkenylsulfonate, and ligand.

9. The device according to claim 8, wherein said silicone precursor, comprises:
 a first component having silicone prepolymer with reactive vinyl groups and metal catalyst; and
 a second component having silicone prepolymer with reactive vinyl groups and prepolymer having Si—H groups.

10. The device according to claim 8, wherein the sodium C$_{3-28}$ alkylsulfonate or alkenylsulfonate comprises sodium C$_{12-14}$ alkenyl sulfonate.

11. The device according to claim 8, wherein the ligand is 15-crown-5 ether.

12. The device according to claim 8, wherein the method, comprises:
 mixing 40 to 98.5% by weight of the silicone precursor with 1 to 30% by weight of the sodium C$_{3-28}$ alkylsulfonate or alkenylsulfonate, and up to 30% by weight of the ligand to form a mixture.

13. An aqueous fluid absorbing, non-medical or non-health care device, comprising:
a rubbery or elastomeric polymer material effective to take up more than 40% by weight and up to 500% by weight of water after immersion in demineralized water at room temperature for a sufficient time to reach saturation, of the formula I:

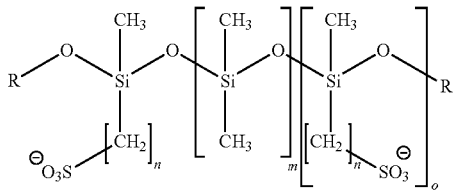

R = Si(CH$_3$)$_3$ or H wherein, R is Si(CH$_3$)$_3$ or hydrogen, n is from 3 to 28, and (m+o+1) is at least 5 and less than 1,000,
said polymer material, comprising:
(a) repeating units from one or more hydrophobic organic monomers;
(b) repeating units from the one or more monomers being modified with C$_{3-28}$ alkylsulfonate or alkenylsulfonate side groups in association with a cation selected from the group consisting of ammonium, Li, Na and K, Ca and Mg, and the repeating units (b) constituting from 1% to 30% of a total number of repeating units (a) and repeating units (b); and
a detectable trace of a ligand selected from the group consisting of crown ether, cryptand and calixerene.

14. A non-medical device according to claim 13, being selected from the group consisting of external and in-ear head sets, ear clips, nose and/or ear pieces of glasses, handles, textile and non-textile parts of shoes, building elements made of metal or plastic, parts of boats, printing stamps, clothing textiles, cosmetic compositions, printing inks, toner compositions, paint or coating compositions, surfactant compositions, antifoaming agents, rolling oil formulations, wafer bonding agents, anti-statics, developers for lithographic plates, artificial sponges, anti-fog agents, nonwoven articles, body contact belts and bands, seats, highly reflective products, sliding transportation systems, sliding sealing rings, and oil barriers in silicone rings.

* * * * *